United States Patent [19]

Kleber et al.

[11] 4,294,990
[45] Oct. 13, 1981

[54] ALKYL-POLYGLYCOL MIXED FORMALS AS FIBER PREPARATION AGENTS

[75] Inventors: Rolf Kleber, Neu-Isenburg; Siegfried Billenstein, Burgkirchen, both of Fed. Rep. of Germany

[73] Assignee: Hoechst Aktiengesellschaft, Fed. Rep. of Germany

[21] Appl. No.: 21,978

[22] Filed: Mar. 19, 1979

[30] Foreign Application Priority Data

Mar. 22, 1978 [DE] Fed. Rep. of Germany ....... 2812443

[51] Int. Cl.³ ............................................ D06M 13/18
[52] U.S. Cl. ..................................... 568/601; 252/8.9
[58] Field of Search .................. 252/8.9; 568/672, 601

[56] References Cited

U.S. PATENT DOCUMENTS 3,926,816 12/1975 Cohen et al. ......................... 252/8.9
3,997,450 12/1976 Steinmiller ........................... 252/8.9

FOREIGN PATENT DOCUMENTS 50-101693 8/1975 Japan.
1125715 8/1968 United Kingdom ................ 568/601

OTHER PUBLICATIONS

Chem. Abs. 84:32514w, "Lubricants for Fibers", Japan Kobai 75,101,693, Kobayashi et al. (Jeijin Ltd.).
Translation of Japanese Kokai Patent 50-101693, Pub. 8-12-75, Koboyashi et al, "Oil for Treating Fibers" (U.S. P.T.O. Ishimoto).

Primary Examiner—John C. Bleutge
Assistant Examiner—Herbert T. Lilling
Attorney, Agent, or Firm—Connolly and Hutz

[57] ABSTRACT

A fiber preparation containing or consisting of a polyglycol ether mixed formal of the formula $$R_1-(OC_2H_4)_n-OCH_2OCH_2CH_2OR_2$$

in which $R_1$ is a linear or branched alkyl or alkenyl radical of from 8 to 22 carbon atoms, $R_2$ is a linear alkyl radical of from 1 to 4 carbon atoms and n is an integer of from 3 to 30.

2 Claims, No Drawings

ALKYL-POLYGLYCOL MIXED FORMALS AS FIBER PREPARATION AGENTS

The present invention relates to alkyl-polyglykol mixed formals as fiber preparation agents.

The use of mineral oils in the preparation of synthetic fibers is well-known. In a similar manner there are also used as inert lubricants ester oils, such as butyl stearate, sterically hindered esters, such as trimethylolpropane tridecylate, and others (Chemiefasern/Textilindustrie 27/79 (1977), pages 322 to 328). U.S. Pat. No. 3,997,450 describes as fiber preparation agents oxethylates having blocked terminal hydroxyl groups, for example, oxethylates carrying methyl terminal groups. The former oxethylates are also claimed in German Offenlegungsschrift No. 1,594,906 for the preparation and oiling of fully synthetic and cellulose ester filaments. "The International Dyer and Textile Printer" (1965), pages 343 to 346 also describes the use of oxethylates having blocked terminal hydroxyl groups in the fiber preparation composition. Compared with the oxethylates having free terminal hydroxyl groups, the above oxethylates with blocked terminal hydroxyl groups have the advantage of showing a greater thermostability, and they do not swell up the yarns or the equipment for the fiber preparation (U.S. Pat. No. 3,997,450, column 1, lines 62 et seq.). This is why in modern texturizing compositions the oxethylates having blocked terminal hydroxyl groups have gained an important share in the market. A serious drawback of the known oxethylates having blocked terminal hydroxyl groups, as they are claimed for example in German Offenlegungsschrift No. 1594906 as ethers of oxethylates, is to be seen in their low chemical reactivity. Thus, the methyl ether of, for example, coconut oil alcohol×6EO is difficult to further react chemically, so that the blocking of the terminal hydroxyl group leads to an inert derivative. As is well-known, a splitting off of the terminal methyl group can only be effected with difficulty.

The objective which was most interesting in practice was method to obtain oxethylates having blocked terminal hydroxyl groups, which do not swell up the filament and, for example, texturizing reels, which impart to the filament optimum friction properties, and which may easily be split chemically. Besides, said derivatives were required to show the same favorable properties in waste water as the free oxethylates themselves.

It has now been found that as lubricants for the fiber preparations there may be used polyglycol ether mixed formals of the general formula I $$R_1-(OC_2H_4)_n-OCH_2OCH_2CH_2OR_2$$

in which
$R_1$ represents a linear or branched alkyl or alkenyl chain with from about 8 to 22 carbon toms, preferably the coconut oil alkyl radical, $R_2$ is a linear radical with from 1 to 4 carbon atoms, preferably methyl, an n stands for a number of from 3 to 30, preferably from 5 to 15.

These compounds are prepared according to the processes described in German Offenlegungsschrift No. 2,523,588, by reacting a fatty alcohol oxethylate of the formula $R_1-(OC_2H_4)_nOH$ with a di-alkyl-glycol formal of the formula $CH_3(OC_2H_4OR_2)_2$ in the presence of a strong acid, while simultaneously removing the glycol-monoalkyl ether which is also formed in the course of this process. These mixed formals are stable in the alkaline medium, but they can be split easily in the acid medium.

Due to their unexpected low filament/metal friction, which manifests itself as a favorable sliding effect, the compounds of the above formula I are very well suitable as lubricants. The application of these mixed formals is effected according to the common methods, for example by slop-padding, dipping or spraying. Said compounds may be applied onto the fiber in their pure form or from a diluted aqueous solution. Since the mixed formals are soluble in water, no additional emulsifying agents are required in contrast with the mineral and ester oils. The components which are common in the fiber preparation, for example antistatic agents and agents effecting a compactness of the thread, may also be admixed to these mixed formals. As the fiber types which may be conditioned with these mixed formals there may be mentioned all synthetic and natural fibers, such as cellulose, polyester, polyacrylonitrile or polyamide. The amount of active substance applied on the fiber is from about 0.5 to 1.5% by weight for beaming and weaving preparations and from about 0.3 to 0.8% by weight for texturizing preparations. The mixed formals may also be employed as anhydrous formulations for coning oils or for after-finish preparations and other treatment processes. In these cases the amount of active substance applied is from about 1 to 5% by weight for coning oils and from about 0.3 to 0.8% by weight for the final brightening. Due to their instability in the acid pH range these preparations can easily be destroyed by adjusting the waste water to a slightly acid value after washing out the preparation agent. The cleavage products being formed are readily degradable biologically. In some cases it is already sufficient to pass air through the waste water, ion order to split the mixed formals.

Preparation of the mixed formals. 446 Grams (1 mol) of a reaction product of 1 mol of a $C_{12/14}$ fatty alcohol with 5 mols of ethylene oxide, 410 g (2.5 mols) of di-(methylglycol)-formal and 3 g of concentrated sulfuric acid are introduced together into a stirring flask having a capacity of 2 liters and being provided with a thermometer, and said substances are stirred for about 5 to 6 hours at a reaction temperature of about 150° C. At the same time a very slight nitrogen current is passed over the mixture. Said mixture is cooled to a temperature of 90° to 100° C., and the acid catalyst proportions contained in the reaction mixture are neutralized with NaOH powder.

Subsequently the excess di-(methylglycol)-formal and the methylglycol formed are distilled off up to an internal temperature of about 100° C. to 15 to 20 mbars. The final product remaining as distillation sump is freed by filtration from the salts contained therein. There are obtained 510 g (96% of the theory) of the compound (a) of the formula $$R-(OC_2H_4)_5-OCH_2OC_2H_4OCH_3$$

in which R is the mixture of the alkyl groups which is present in the coconut oil acid. The residual hydroxyl number was 15. At 20° C. the product is a limpid liquid which is easily soluble in cold water.

In a similar manner the following products are prepared:
(b) $C_{12/14} \times (EO)_4-O-CH_2-CH_2CH_2-O-C_4H_9$
(c) $C_{16/20} \times (EO)_3-O-CH_2-O-CH_2CH_2-O-C_3H_7$ (d) $C_{12/14} \times (EO)_8$—O—$CH_2$—O—$CH_2CH_2$—O—$CH_3$ (e) $C_{12/14}$—$(EO)_5$—O—$CH_2$—$nC_4H_9$: comparison product according to German Offenlegungsschrift No. 2,523,588

(f) $C_{12/14} \times (EO)_5$—O—$CH_2$—$nC_4H_9$: comparison product according to German Offenlegungsschrift No. 3,997,450

(g) $C_{12/15}$—oxoalcohol $\times (EO)_4$—O—$CH_2$—O—$CH_2$—$CH_2$—O—$CH_2$ (according to the invention)

(h) $C_{12/15}$—oxoalcohol $\times (EO)_3$—O—$CH_2$—O—$CH_2$—$CH_2$—O—$C_2H_5$ (according to the invention)

The above-described products were applied from an aqueous solution (concentration of 1% of active substance) with a concentration of 0.7% of active substance onto a PA-6 filament (dtex 220 f 40) and were tested for their sliding friction (filament/metal friction) after drying in accordance with the method indicated in German Offenlegungsschrift No. 2,355,675).

At 25 m and a measuring rate of 100 m/minute, the following values were measured:

Product a: 0.205 to 0.270
Product b: 0.210 to 0.280
Product c: 0.212 to 0.278
Product d: 0.225 to 290
Product e: 0.240 to 0.310 (comparison)
Product f: 0.230 to 0.305 (comparison)
Product g: 0.215 to 0.285
Product h: 0.220 to 0.280

The friction values of the alkyl-glycol mixed formals of the invention were always lower than the values of the comparison products.

In order to test the stability of products (a) to (h), aqueous baths were prepared which had a content in each case of 10 g/l of the products (a) to (h). The baths were adjusted to a pH value of 2, and the formation of free oxethylated alcohol in the bath was followed at 50° C. It became evident that all alkyl-glycol mixed formals are completely saponified within 24 hours, whereas product (f) remains stable. Product (e) is degraded quantitatively within 10 hours, however, while showing the highest frichtion value measured of all compounds.

What is claimed is:

1. A polyglycol ether mixed formal of the formula

$$R_1-(OC_2H_4)_n-OCH_2OCH_2CH_2OR_2$$

in which $R_1$ is a linear or branched alkyl or alkenyl radical of from 8 to 22 carbon atoms, $R_2$ is a linear alkyl radical of from 1 to 4 carbon atoms and n is an integer of from 3 to 30.

2. A polyglycol ether mixed formal of claim 1 wherein $R_1$ is alkyl derive from coconut fatty acid, $R_2$ is methyl and n is an integer of from 5 to 15.

* * * * *